United States Patent
Thaning, Jr. et al.

(10) Patent No.: US 9,884,808 B2
(45) Date of Patent: Feb. 6, 2018

(54) PREPARATION OF AN INTERMEDIATE COMPOUND OF IOFORMINOL

(71) Applicant: GE Healthcare AS, Oslo (NO)

(72) Inventors: Mikkel Jacob Thaning, Jr., Oslo (NO); Andreas Olsson, Oslo (NO); Christian Glogard, Oslo (NO)

(73) Assignee: GE Healthcare AS, Oslo (NO)

( * ) Notice: Subject to any disclaimer, the term of this patent is extended or adjusted under 35 U.S.C. 154(b) by 0 days.

(21) Appl. No.: 14/430,155

(22) PCT Filed: Sep. 17, 2013

(86) PCT No.: PCT/US2013/060081
§ 371 (c)(1),
(2) Date: Mar. 20, 2015

(87) PCT Pub. No.: WO2014/052091
PCT Pub. Date: Mar. 4, 2014

(65) Prior Publication Data
US 2015/0246871 A1  Sep. 3, 2015

(30) Foreign Application Priority Data

Sep. 27, 2012 (NO) .................................. 20121102

(51) Int. Cl.
| C07C 231/14 | (2006.01) |
| C07C 231/02 | (2006.01) |
| C07C 231/24 | (2006.01) |
| C07C 237/46 | (2006.01) |

(52) U.S. Cl.
CPC .......... *C07C 231/14* (2013.01); *C07C 231/02* (2013.01); *C07C 231/24* (2013.01); *C07C 237/46* (2013.01)

(58) Field of Classification Search
CPC ........................... C07C 231/14; C07C 237/46
See application file for complete search history.

(56) References Cited

U.S. PATENT DOCUMENTS

| 6,974,882 B2 | 12/2005 | Homestad |
| 8,445,724 B2 | 5/2013 | Cervenka et al. |
| 8,829,241 B2 | 9/2014 | Cervenka et al. |
| 8,920,780 B2 | 12/2014 | Thaning |
| 2015/0265727 A1* | 9/2015 | Thaning ............. A61K 49/0438 424/9.452 |

FOREIGN PATENT DOCUMENTS

| EP | 0108638 A1 | 5/1984 |
| EP | 0855997 A1 | 8/1998 |
| EP | 1150943 B1 | 9/2003 |
| EP | 1924541 A1 | 5/2008 |
| EP | 1778621 B1 | 6/2012 |
| EP | 2178568 B1 | 7/2014 |
| EP | 2900632 A1 | 8/2015 |
| JP | 11-502231 A | 2/1999 |
| JP | 2002-536429 A | 10/2002 |
| JP | 2008-509214 A | 3/2008 |
| JP | 2009-502910 A | 1/2009 |
| JP | 2010-533172 A | 10/2010 |
| WO | 1997/000240 A1 | 1/1997 |
| WO | 1998/023296 A1 | 6/1998 |
| WO | 0047549 A1 | 8/2000 |
| WO | 2006016815 A1 | 2/2006 |
| WO | 2007/013815 A1 | 2/2007 |
| WO | 2009008734 A2 | 1/2009 |
| WO | 2014/052091 A1 | 4/2014 |

OTHER PUBLICATIONS

Bandgar et al., Clean and Green Approach for N-formylation of Amines using Formic acid under neat reaction condition, Archives of Applied Science Research, vol. 3, No. 3, 2011, 6 pages.
International Search Report and Written Opinion for PCT/US2013/060081, dated Dec. 6, 2013, 10 pages.
Ogata, Akira, "Chemical Experiment Operating Method", vol. 1, 27th Edition, Nov. 20, 1963, pp. 366-399.
The Chemical Society of Japan, 2003, 3 pages.
International Preliminary Report on Patentability Received for PCT Application No. PCT/US2013/060081, dated Apr. 9, 2015, 6 Pages.
Office Action Received for Japanese Patent Application No. 2015534549, dated Jul. 18, 2017, 11 Pages (5 Pages of English Translation + 6 pages of Official copy).
Chai et al., "Predicting Cardiotoxicity Propensity of the Novel Iodinated Contrast Medium GE-145: Ventricular Fibrillation During Left Coronary Arteriography in Pigs", Acta Radiologica, vol. 51, Issue 9, 2010, pp. 1007-1013.
Wistrand et al. "GE-145, A New Low-Osmolar Dimeric Radiographic Contrast Medium", Acta Radiologica, vol. 51, Issue 9, 2010, pp. 1014-1020.

* cited by examiner

*Primary Examiner* — Jafar Parsa
*Assistant Examiner* — Amy C Bonaparte
(74) *Attorney, Agent, or Firm* — Wood IP LLC

(57) ABSTRACT

The present invention relates to a process for the preparation of iodinated X-ray contrast agents and in particular to key intermediates thereof. More particularly, the invention relates to a work-up process for preparation of a compound mixture comprising 1-formylamino-3,5-bis(2,3-bis(formyloxy)propan-1-ylcarbamoyl)-2,4,6-triodobenzene, a key intermediate in the process for preparing Ioforminol. Further, the invention relates to a process for preparing Ioforminol, a contrast agent useful in X-ray imaging.

19 Claims, No Drawings

PREPARATION OF AN INTERMEDIATE COMPOUND OF IOFORMINOL

This application is a filing under 35 U.S.C. 371 of international application number PCT/US2013/060081, filed Sep. 17, 2013, which claims priority to Norwegian application number 20121102, filed Sep. 27, 2012, the entire disclosures of each of which are hereby incorporated by reference.

The present invention relates to a process for the preparation of iodinated X-ray contrast agents and in particular to key intermediates thereof. More particularly, the invention relates to preparation of a compound mixture comprising 1-formylamino-3,5-bis(2,3-bis(formyloxy)propan-1-ylcarbamoyl)-2,4,6-trioodobenzene, a key intermediate in the process for preparing Ioforminol. Further, the invention relates to a process for preparing Ioforminol, a contrast agent useful in X-ray imaging.

For the last 50 years the field of X-ray contrast agents has been dominated by soluble iodine containing compounds. Commercial available contrast media containing iodinated contrast agents are usually classified as ionic monomers such as diatrizoate (Gastrografen™), ionic dimers such as ioxaglate (Hexabrix™) nonionic monomers such as iohexol (Omnipaque™), iopamidol (Isovue™), iomeprol (Iomeron™) and the non-ionic dimer iodixanol (Visipaque™). The most widely used commercial non-ionic X-ray contrast agents such as those mentioned above are considered safe. Contrast media containing iodinated contrast agents are used in more than 20 million of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The part of the patient population considered as high risk patients is increasing. To meet the need for continuous improvement of in vivo X-ray diagnostic agents for the entire patient population, there is a continuous drive in finding X-ray contrast agents that have improved properties, also with regards to contrast induced nephrotoxicity (CIN).

X-ray contrast media containing a chemical compound as the active pharmaceutical ingredient(s) having two triiodinated phenyl groups linked by a linking group are usually referred to as dimeric contrast agents or dimers. During the years a wide variety of iodinated dimers have been proposed. Currently, one contrast medium having an iodinated non-ionic dimer as the active pharmaceutical ingredient is on the market, the product Visipaque™ containing the compound iodixanol.

In WO2009/008734 of the applicant a novel dimeric contrast agent named Ioforminol is disclosed. The properties of this is described in more detail in the publications Chai et al. "Predicting cardiotoxicity propensity of the novel iodinated contrast medium GE-145: ventricular fibrillation during left coronary arteriography in pigs", Acta Radiol, 2010, and in Wistrand, L. G., et al "GE-145, a new low-osmolar dimeric radiographic contrast medium", Acta Radiol, 2010. Ioforminol (GE-145) is named Compound 1 herein and has the following structure:

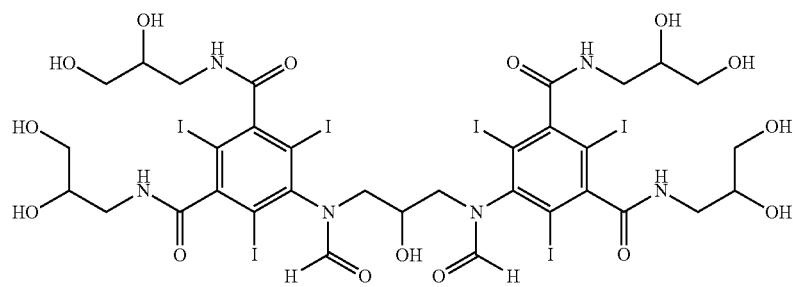 [SMILES: O=CN(CC(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

Compound 1:
5,5'-(2-Hydroxypropane-1,3-diyl)bis(formylazanediyl)bis(N$^1$,N$^3$-bis(2,3-dihydroxypropyl)-2,4,6-triiodoisophthalamide)

The manufacture of non-ionic X-ray contrast media involves the production of the chemical drug, the active pharmaceutical ingredient (API), i.e. the contrast agent, followed by the formulation into the drug product, herein denoted the X-ray composition. WO2009/008734 of the applicant provides a synthetic route for preparing the API Ioforminol. Ioforminol can e.g., as provided by the general preparation description and Example 1 of WO2009/008734, be synthesized from 5-amino-N,N'-bis-(2,3-dihydroxy-propyl)-2,4,6-triiodo-isophthalamide (compound (4)), which is commercially available. The preparation of this compound is known from the synthesis of both iohexol and iodixanol and can also be prepared from 5-nitroisophthalic acid for instance as described in WO2006/016815, including hydrogenation and subsequent iodination e.g. by iodine chloride, ICl. Alternatively, 5-amino-2,4,6-triiodoisophthalic acid may be used, which is commercially available precursor, e.g. from Sigma-Aldrich. The free amino group of the isophthalamide compound (compound (4)) is then acylated and the hydroxyl groups in the substituents may also be protected by acylation. The protecting groups may be removed for example by hydrolysis to give N$^1$,N$^3$-bis(2,3-dihydroxypropyl)-5-formylamino-2,4,6-triiodoisophthalamide. In a dimerization step this is reacted e.g. with epichlorohydrin to provide the Ioforminol contrast agent compound.

The state of the art synthesis of Ioforminol, as disclosed in examples 1 and 2 of WO2009/008734, is shown in Scheme 1 below.

Scheme 1.

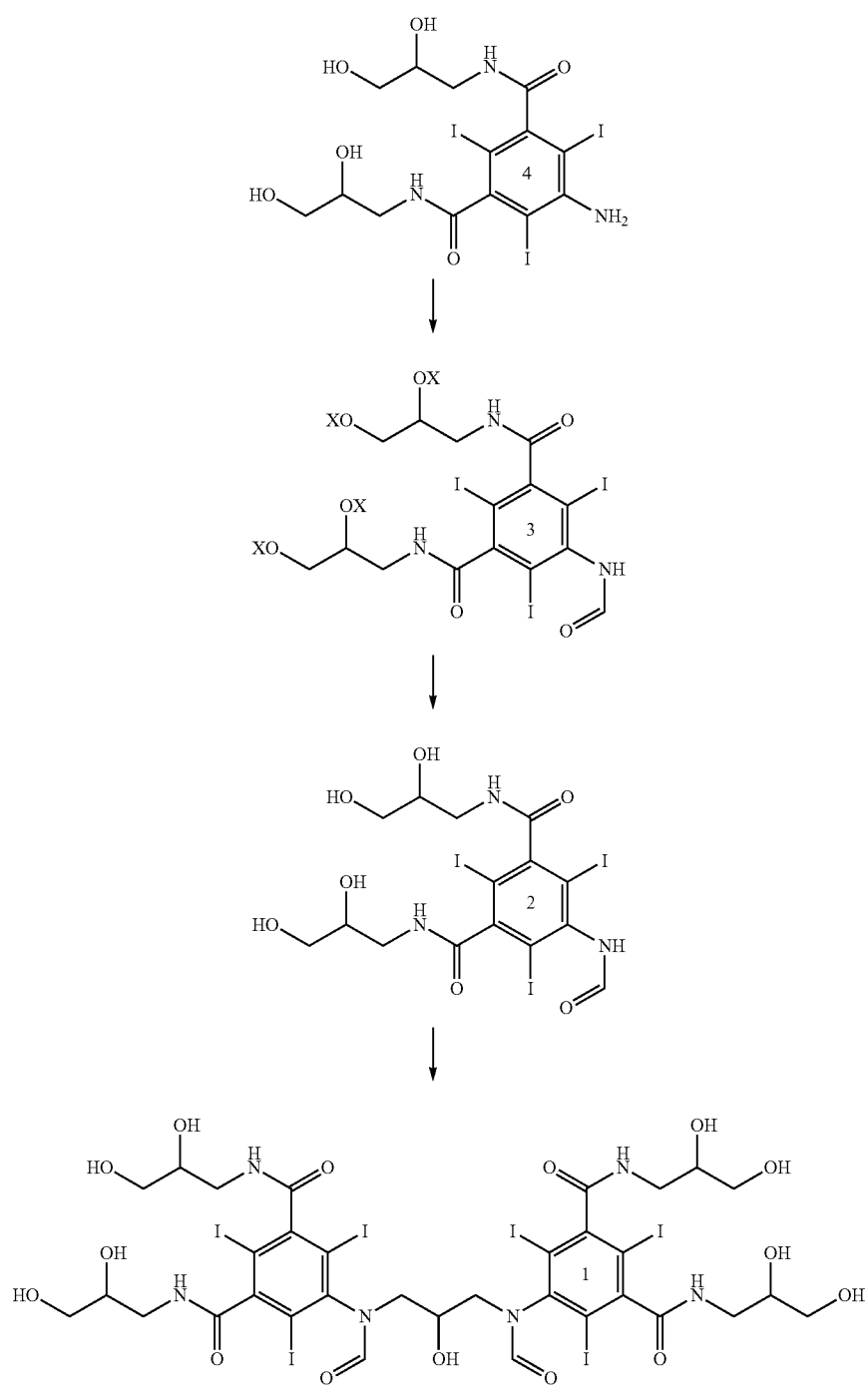

As described in WO2009/008734 compound 3 is a mixture comprising 1-formylamino-3,5-bis(2,3-bis(formyloxy) propan-1-ylcarbamoyl)-2,4,6-trioodobenzene, and X is then a formyl group.

In each synthetic step it is important to optimize the yield and minimize the production of impurities. The problem to be solved by the present invention may be regarded as the provision of optimizing the process for preparation of compound mixture (3) of scheme 1, i.e. a mixture comprising 1-formylamino-3,5-bis(2,3-bis(formyloxy)propan-1-ylcarbamoyl)-2,4,6-trioodobenzene. The process is hence directed to the preparation of compound mixture (3) by the formylation of the amino function of 5-amino-$N^1,N^3$-bis(2, 3-dihydroxypropyl)-2,4,6-triiodoisophthalamide (4), including a work-up procedure.

In the state of the art process, as disclosed in WO2009/ 008734, Example 2, procedure B, 1-formylamino-3,5-bis(2, 3-bis(formyloxy)propan-1-ylcarbamoyl)-2,4,6-trioodobenzene (compound 3 wherein X is a formyl-group) is prepared by formylation of compound (4) using formic acid and acetic anhydride. The reaction mixture was evaporated in vacuum to a moist mass which was further dried in vacuum. The product was used in the next step without purification. The work up process of the state of the art hence consisted of a concentration of the reaction mixture to dryness under reduce pressure, and the product was recovered as a plaster like material with a high content of formic acid and acetic acid. A challenge with this work-up process has been the removal of formic acid and acetic acid from the reaction suspension which is difficult due to their high boiling points. The hard lumpy material obtained by the state of the art process was difficult to purify and also needed milling before the next synthetic step.

An improved work-up process has been sought for preparation of the acylated compound mixture (3) from compound (4), wherein the product is obtained in powder form in a high yield and of high purity. We have now found that compound mixture (3) can be prepared in powder form in high purity and high yield by performing a work-up procedure wherein a short chain alcohol is used as an antisolvent. It has been found that by using such alcohol as an antisolvent compound mixture (3) can be crystallised out of the solution in high yields allowing for a filtration work-up.

Accordingly, in a first aspect the invention provides a process for preparation of compound mixture (3) as a powder

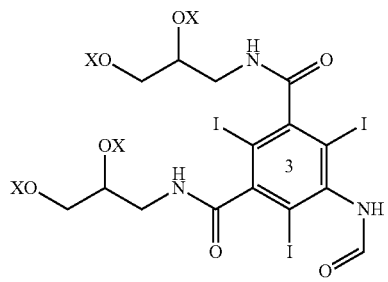

Compound mixture 3
wherein each X individually denotes hydrogen, a formyl group (—CO—H) or an acetyl group (—CO—CH$_3$)
the process comprises the steps of:
i) formylating the amino function of 5-amino-N$^1$,N$^3$-bis (2,3-dihydroxypropyl)-2,4,6-triiodoisophthalamide (compound (4));
ii) performing a work-up procedure wherein a short chain alcohol is added to the product solution of step i).

In the synthetic step i) the free amino function of the iodinated phenyl group of compound (4) is formylated to prepare the corresponding formanilide group. The formylation may be effected by any convenient method, e.g. by use of activated formic acid such as mixed anhydrides as the formylating agent, which can be prepared by a variety of methods described in the literature. A convenient method of preparing mixed anhydrides is to add a carboxylic acid anhydride to an excess of formic acid under controlled temperature. Preferably, a mixture of formic acid and acetic anhydride is used in this step. Preferably, formic acid is cooled, e.g. to 8-15° C., such as to about 10° C., and acetic acid anhydride is added slowly, such as drop wise, keeping the temperature down, such as below about 15° C. As the formation of mixed anhydride is an exothermic reaction, and high temperatures decompose the anhydrides, the reagents should be cooled prior to mixing. This mixed anhydride solution may then be added to the compound (4), which is preferably solved in formic acid. Alternatively, compound (4) is added to the mixed anhydride solution. It is also possible to make mixed anhydrides by addition of a carboxylic acid chloride to a solution of a formic acid salt. Formyl-mixed anhydrides may include acetyl, isobutyryl, pivaloyl, benzoyl etc.

As a result of the formylating step (i) using mixed anhydrides, compound mixture (3) will be a mixture of different compounds with both formyl and acetyl protecting groups. Varies degree of O-formylation is seen, but a high degree of N-formylation takes place, ensuring a high yield of the N-formylated compound mixture (3). In one embodiment compound mixture (3) comprises a mixture of compounds wherein all X groups are individually formyl or acetyl. The main component of compound mixture (3) is 1-formylamino-3,5-bis(2,3-bis(formyloxy)propan-1-ylcarbamoyl)-2,4,6-trioodobenzene.

When using the work-up procedure of the invention, compound mixture (3) can be recovered by filtration as a fine powder with low acid content. The short chain alcohol has several functions in the procedure; it is initially used to quench excess anhydride in the reaction solution, in addition to that it acts as an antisolvent that lowers the solubility and crystallizes compound mixture (3). The crystallisation gives small crystals that aggregate into robust clusters that give an excellent rapid filtration, and an easy wash of the crystals. The work-up procedure has been repeated multiple times and provides yields of the N-formylated compound mixture (3) above 95%, more preferably above 98%, and most preferably 99% or above, in both small scale and large scale, such as in 100 kg scale. The main impurity is the N-acylated compound in approx. 0.5% abundance.

The short chain alcohol used in step (ii) is selected from C1-C6 straight or branched alcohols and may be a mixture of such. The alcohol may be monohydroxylated or dihydroxylated. Methanol, ethanol and propanols are preferred alcohols, with propanols, particularly iso-propanol, being most preferred.

After step i) has been performed, i.e. when all the formylating agent has been added to the compound (4) solution, this reaction solution is preferably kept at a low temperature, such as 10-40° C., e.g. about 15° C., under stirring for a period to allow the reaction to completion, such as for at least an hour. In one embodiment, this reaction solution is seeded with compound mixture (3) and left under stirring for an additional period, such as for one hour or more. In step ii) the alcohol is then added carefully to the reaction solution to quench any excess anhydride and to lower the solubility of compound mixture (3), to provide a thicker suspension. This suspension is preferably left under stirring at ambient temperature. It has been found useful adding the alcohol as an antisolvent in a concentration of about 0.3 to about 2.0 ml per gram of compound (4). More preferably the concentration is about 0.5-1.0 ml per gram of compound (4), and most preferably 0.6-0.7 ml per gram of compound (4).

To provide a complete precipitation the reaction slurry of step (ii) is left under stirring for a period of e.g. 5-25 hours, such as 10-20 hours before compound mixture (3) is collected and optionally purified. In one embodiment the process comprises such further step of collecting the product preferably by filtration, e.g. by using a nutch filter, such as a vacuum nutch filter or pressure nutch, or a combination thereof, also optionally combined with heating. The product is preferably subsequently washed with a short chain alcohol, preferably the same alcohol as used in step (ii), in one or more portions, such as in 1 to 5 portions and preferably with 3 portions providing compound mixture (3) as a dense white powder, optionally being vacuum-dried. The amount of alcohol used in the washing may be about the same amount as used in the precipitation, divided on the number of portions. It has been found that it is beneficially for the further synthesis that some alcohol is left in the compound mixture (3) after the work-up procedure has finished, hence the drying should be adjusted accordingly. Preparation of compound mixture (3) with a rest alcohol content of 0-7% has been found appropriate.

The compound mixture (3) as provided by the process of the invention is a dense white powder, in contrast to the hard lumpy material that was obtained by the state of the art process. In a further aspect the invention provides compound mixture (3) as a white powder, preferably prepared according to the process of the first aspect.

Processes which take the compound mixture (3) as prepared by the claimed process and react this further, e.g. to produce Ioforminol, are deemed to fall within the scope of the invention. Hence, in a further aspect the invention provides a process for preparing Ioforminol comprising the work-up procedure for preparation of compound mixture (3) as described in the first aspect. Such process could comprise the additional steps of removal of the protecting groups of compound mixture (3) and dimerization to provide Ioforminol. The protecting acyl groups (formyl and acetyl) of compound mixture (3) may conveniently be removed by standard methods, for example by hydrolysis, such as in aqueous basic media, or by alcoholysis.

In a final step for preparation of Ioforminol a bis alkylation via a 2-hydroxypropane bridge takes place. This step may be carried out as described in European patent 108638 and WO 98/23296, for example using epichlorohydrin, 1,3-dichloro-2-hydroxypropane or 1,3-dibromo-2-hydroxypropane as the dimerization agent. This dimerization is preferably effected in the presence of an acid binding agent, for example an organic or inorganic base; an alkali metal alkoxide such as sodium methoxide or an alkali metal hydroxide such as sodium and potassium hydroxide may be used as base.

Compound mixture (3) and compound (1) as prepared by the claimed process comprise optical active isomers and will exist in several isomeric forms due to chiral carbon atoms. In addition, the compounds exhibit exo/endo isomerism due to the restricted rotation of the N—CO bond in the formyl function caused by the proximity of the bulk iodine atom. Both preparation of enantiomerically pure products as well as mixtures of optical isomers are encompassed by the process of the invention.

The compounds prepared, such as compounds (1), (2) and (3), may be purified in any convenient manner, e.g. by preparative chromatography, by recrystallization or ultra/nano-filtration.

The compounds prepared according to the invention may be used as contrast agents and may be formulated with conventional carriers and excipients to produce diagnostic contrast media. Thus viewed from a further aspect the invention provides a diagnostic composition comprising Ioforminol prepared according to the process of the invention, together with at least one physiologically tolerable carrier or excipient, e.g. in aqueous solution for injection optionally together with added plasma ions or dissolved oxygen. The contrast agent composition of the invention may be in a ready to use concentration or may be a concentrate form for dilution prior to administration. Hence, the invention further embraces use of Ioforminol prepared according to the process of preparation, and a diagnostic composition containing such, in X-ray contrast examinations.

The invention is illustrated with reference to the following non-limiting examples.

EXAMPLES

Example 1: Preparation of compound mixture (3) comprising 1-formylamino-3,5-bis(2,3-bis(formyloxy)propan-1-ylcarbamoyl)-2,4,6-trioodobenzene 5-amino-N1,N3-bis(2,3-dihydroxypropyl)-2,4,6-triiodo-isophthalamide (compound (4)) (7.5 kg, 10.6 moles) was dissolved in formic acid (4.9 l) and heated to 45° C. until a clear solution was obtained (~4 hours), then the thick amber solution was cooled to 10° C.

Formic acid (9.4 l) was charged into a different reactor and cooled to 10° C., after reaching the target temperature acetic anhydride was added at such a rate that the temperature did not exceeded 15° C.

After 2.5 hours all acetic anhydride was added to the formic acid and the mixed anhydride solution was added drop wise to the compound (4) solution. The rate of addition was adjusted so that the temperature never exceeded 20° C. After 2 hours all mixed anhydride had been added and the reaction was left stirring at 15° C. for additional 1 hour. Isopropanol (4.9 l) was added carefully and the suspension became noticeable thicker and was left stirring at ambient temperature. After 16 hours the reaction slurry was filtered on a vacuum nutch and washed with isopropanol (3*1.5 l) to give compound mixture (3) comprising 1-formylamino-3,5-bis(2,3-bis(formyloxy)propan-1-ylcarbamoyl)-2,4,6-trioodobenzene as a dense white powder (7.98 kg). The quantitative yield with regards to N-formylation was >99%.

The invention claimed is:

1. A process for the preparation of a compound mixture (3) as a powder, wherein the compound mixture (3) comprises two or more compounds of formula (3)

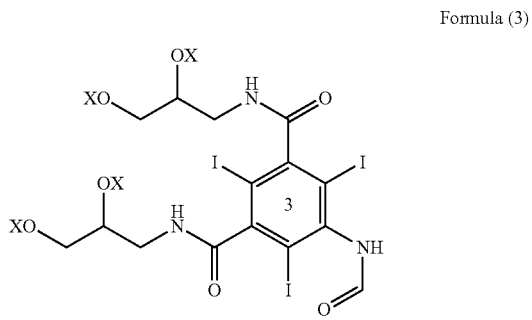

Formula (3)

wherein each X individually denotes hydrogen, a formyl group (—CO—H) or an acetyl group (—CO—CH$_3$), said process comprising:
i) formylating the amino function of 5-amino-N$^1$,N$^3$-bis(2,3-dihydroxypropyl)-2,4,6-triiodoisophthalamide (compound (4)) in the presence of a mixed anhydride comprising an acetyl group to form a product solution;
ii) adding isopropanol in situ to the product solution of step i) to form a slurry comprising precipitated compound mixture (3), wherein the concentration of isopropanol is about 0.5 to 1.0 mL per gram of compound (4) and the slurry of step (ii) is stirred for 5-25 hours; and iii) collecting the precipitated compound mixture (3) by filtration.

2. The process of claim 1, further comprising seeding the product solution of step i) with compound mixture (3) before adding isopropanol.

3. The process of claim 1, wherein the concentration of the isopropanol is about 0.6 to about 0.7 ml per gram of compound (4).

4. The process of claim 1, wherein the amount of isopropanol used in step ii) is added in one portion and the process further comprises a step of washing the compound mixture (3) collected in step iii) with one or more portions of isopropanol.

5. The process of claim 1, wherein the compound mixture (3) prepared by the process has a purity of >99%.

6. A process for preparing Ioforminol from a compound mixture (3), the process comprising preparing compound mixture (3) according to the process of claim 1, hydrolyzing compound mixture (3) to form a compound (2), wherein all X in formula (3) are H, and dimerizing compound (2) to form Ioforminol.

7. The process of claim 1, wherein the slurry of step ii) is stirred for 10-20 hours.

8. The process of claim 1, wherein the compound mixture (3) comprises 0-7 wt % isopropanol.

9. A process for the preparation of a compound mixture (3) as a powder, wherein the compound mixture (3) comprises two or more compounds of formula (3)

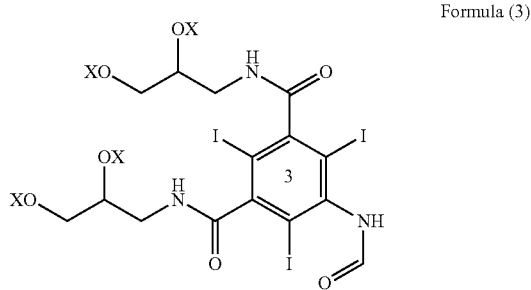

Formula (3)

wherein each X individually denotes hydrogen, a formyl group (—CO—H) or an acetyl group (—CO—CH$_3$), said process comprising:

i) formylating the amino function of 5-amino-N$^1$,N$^3$-bis(2,3-dihydroxypropyl)-2,4,6-triiodoisophthalamide (compound (4)) in the presence of a mixed anhydride comprising an acetyl group to form a product solution;

ii) adding a short chain alcohol in situ to the product solution of step i) to form a slurry comprising precipitated compound mixture (3), wherein the concentration of the short chain alcohol is about 0.3 to 2.0 mL per gram of compound (4) and the slurry of step (ii) is stirred for 5-25 hours; and iii) collecting the precipitated compound mixture (3) by filtration;

wherein the short chain alcohol is C1-C6 straight or branched, mono hydroxylated or di hydroxylated, or a mixture thereof.

10. The process of claim 9, further comprising seeding the product solution of step i) with compound mixture (3) before adding the short chain alcohol.

11. The process of claim 9, wherein the concentration of the short chain alcohol is about 0.5 to about 1.0 ml per gram of compound (4).

12. The process of claim 9, wherein the amount of short chain alcohol used in step ii) is added in one portion and the process further comprises a step of washing the compound mixture (3) collected in step iii) with one or more portions of the short chain alcohol.

13. The process of claim 9, wherein the compound mixture (3) in powder form as prepared by the process has a purity of >99%.

14. A process for preparing Ioforminol from a compound mixture (3), the process comprising preparing compound mixture (3) according to the process of claim 9, hydrolyzing compound mixture (3) to form a compound (2), wherein all X in formula (3) are H, and dimerizing compound (2) to form Ioforminol.

15. The process of claim 9, wherein the slurry of step ii) is stirred for 10-20 hours.

16. The process of claim 9, wherein the compound mixture (3) comprises 0-7 wt % short chain alcohol.

17. The process of claim 9, wherein the short chain alcohol is methanol.

18. The process of claim 9, wherein the short chain alcohol is ethanol.

19. The process of claim 9, wherein the short chain alcohol is 1-propanol.

* * * * *